United States Patent
Macciocchi

(10) Patent No.: US 7,394,072 B2
(45) Date of Patent: Jul. 1, 2008

(54) GAMMA CAMERA CALIBRATION AND DIAGNOSIS USING PULSE INJECTION

(75) Inventor: Fred E. Macciocchi, Huntley, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 11/417,811

(22) Filed: May 3, 2006

(65) Prior Publication Data

US 2007/0257193 A1  Nov. 8, 2007

(51) Int. Cl.
  G01T 1/161 (2006.01)
  G01D 18/00 (2006.01)
(52) U.S. Cl. ............... 250/363.09; 250/262.1; 250/363.1; 250/370.11
(58) Field of Classification Search ............ 250/363.09, 250/370.09, 370.11, 252.1
  See application file for complete search history.

(56) References Cited

U.S. PATENT DOCUMENTS

| | | | |
|---|---|---|---|
| 3,011,057 A | 11/1961 | Anger | |
| 4,033,335 A * | 7/1977 | Nickles | 600/436 |
| 4,058,728 A * | 11/1977 | Nickles | 250/369 |
| 4,517,460 A | 5/1985 | Meulenbrugge et al. | |
| 6,080,984 A * | 6/2000 | Friesenhahn | 250/252.1 |
| 6,835,935 B2 | 12/2004 | Engdahl et al. | |
| 6,858,847 B1 | 2/2005 | Macciocchi | |
| 2004/0030227 A1* | 2/2004 | Littrup et al. | 600/300 |
| 2005/0110513 A1* | 5/2005 | Osada et al. | 324/765 |

* cited by examiner

Primary Examiner—David P. Porta
Assistant Examiner—Casey Bryant
(74) Attorney, Agent, or Firm—Peter L. Kendall

(57) ABSTRACT

A quality control system and method are provided for troubleshooting and performance testing of detectors in a Gamma camera that includes a field programmable gate array for forming digital words to be converted to a pulse, a test pattern generator for storing the digital words, a digital analog converter for converting the digital words into an analog voltage, an amplifier for amplifying and applying the analog voltage, and an analog multiplexor for accepting the analog voltage. The Gamma camera comprises a collimator, a scintillation crystal, a light guide, a photomultiplier tube, and an electronic circuit.

13 Claims, 2 Drawing Sheets

GAMMA CAMERA CALIBRATION AND DIAGNOSIS USING PULSE INJECTION

BACKGROUND OF THE INVENTION

1. Field of the Invention

The present invention generally relates to quality control of Gamma cameras in the area of medical diagnostic imaging. In particular, the present invention relates to systems and methods for troubleshooting and performance testing of detectors and other circuitry in a Gamma camera by adding a pulse injection circuit to the Gamma camera.

2. Description of the Background

Gamma cameras are primarily used by doctors who specialize in the field of nuclear medicine. Nuclear medicine is a unique medical specialty wherein Gamma cameras are used in conjunction with very low-level radioactive materials (called radionuclides or radiopharmaceuticals) to generate images of the anatomy of organs, bones or tissues of the body. Gamma cameras can also generate images that can be used to determine whether an organ is functioning properly.

Radionuclides or radiopharmaceuticals are introduced orally or intravenously into the body of a patient. Radiopharmaceuticals are specially formulated to collect temporarily in a certain part of the body to be studied, such as the patient's heart or brain. Once the radiopharmaceuticals reach the intended organ, they emit Gamma rays that are then detected and measured by the Gamma camera. The basic camera sold commercially for nuclear medical imaging is still similar to the original invention by Anger (U.S. Pat. No. 3,011,057, which is incorporated in its entirety by reference herein).

A Gamma camera includes a large area scintillation crystal, which functions as a Gamma ray detector. The crystal is typically sodium iodide doped with a trace of thallium (NaI(Tl)). The crystal converts high-energy photons (e.g., Gamma rays and X-rays) into visible light (i.e., lower energy photons). The crystal is positioned to receive a portion of the Gamma ray emissions from the radiopharmaceuticals.

When a Gamma ray strikes and is absorbed in the scintillation crystal, the energy of the Gamma ray is converted into flashes of light (i.e., a large number of scintillation photons) that emanate from the point of the Gamma ray's absorption in the scintillation crystal. A photo-multiplier tube (PMT), which is optically coupled to the scintillation crystal, detects a fraction of these scintillation photons and produces an output electronic signal (e.g., current or voltage pulse) having an amplitude that is proportional to the number of detected scintillation photons. The Gamma ray camera typically has several photomultiplier tubes placed in a two dimensional array, with the signals from the different photomultiplier tubes being combined to provide an indication of the positions and energies of detected Gamma rays.

The scintillation photons emitted from the detector crystal are typically in the visible light region of the electromagnetic spectrum (with a mean value of about 3 eV for NaI(Tl)). The scintillation photons spread out from the point of emission. A large fraction of the scintillation photons are transported from the point of emission to a light sensitive surface, called the photocathode, of the PMTs. A fraction of the scintillation photons incident on the photocathodes cause an electron to be emitted from the photocathode.

The electron, also called a photoelectron, is then electrostatically accelerated into an electron multiplying structure of the PMT, which causes an electrical current (or voltage) to be developed at an output of the PMT. The amplitude of the electrical signal is proportional to the number of photoelectrons generated in the PMT during the time period that scintillation photons are being emitted. Thus, after a Gamma ray absorption event, the PMT outputs an electrical signal that can be used with other signals from other PMTs to determine the location of the Gamma ray absorption event.

The number of scintillation photons producing electrical signals in each PMT is inversely related to the distance of the PMT from the point of Gamma ray absorption, or event location. It is because of this relationship that the position of the event can be calculated from the signals of the PMTs surrounding the event location.

Ideally, the signal derived from each PMT should have exactly the same proportional relationship to the distance from the event location as for all other PMTs. The amplitudes of the signals derived from each PMT are proportional to two basic factors: 1) the number of scintillation photons detected by a PMT, and 2) the gain or amplification of the PMT. The accuracy to which the position of the event location can be calculated depends on these two factors remaining constant in time.

Typically, a Gamma camera is tuned prior to its operation so as to ensure that the camera will calculate accurately the positions of event locations anywhere within an area called the field of view (FOV). Commercial, large field of view Gamma cameras have between 50 and 100 PMTs. A tuning procedure will typically require a number of steps that balance or equalize the signal amplitudes of the PMTs. The gains of the PMTs are adjusted such that the sum of the signals from all the PMTs is approximately equal in response to a fixed energy Gamma event, regardless of the location of the event.

A known pattern of event locations are presented to the camera, usually by placing a mask of precisely spaced lines or holes over the camera crystal, so that event location calculations can be calibrated to give the known locations fixed by the positions of the holes or slits, where the Gammas can pass through the mask. The exact tuning and/or calibration steps may be different among cameras produced by different manufacturers. However, once the tuning and calibration steps are complete, the image quality, which is incumbent on the camera's ability to accurately position event locations, depends on the transport of scintillation light to the PMTs and the gains of the PMTs remaining unchanged from the time when the tuning and calibration procedures were performed.

A number of factors can cause a change in either the gain of a PMT or the light collection properties of the camera. PMT gain is a strong function of temperature, counting rate (i.e. the number event signals per unit time), and the high voltage (HV) power supply regulation. Additionally, PMTs change their gain over time as they age. The light collection from the crystal to the photocathodes of the PMTs can change if the transmissive properties of surfaces change. For example, the PMTs are optically coupled to a glass or plastic lightpipe using either an optical grease or epoxy. If any of these materials' light transmission properties change, then the transport of scintillation photons to the PMT will change. Additionally, NaI(Tl) is a hygroscopic material, and if water vapor reaches the crystal it becomes yellow and the light transmission is diminished.

Different manufacturers have developed and implemented different means to maintain the constancy of PMT gains. These means fall into two categories: 1) automatic (i.e. not requiring the user to initiate the process), and 2) user quality control procedures (i.e. procedures initiated by the user). Generally, a combination of both automatic and quality control procedures is required.

One known automatic system, for example, utilizes light emitting diodes (LEDs) coupled into the photomultiplier tubes to provide a light signal for calibration of each individual tube. A constant fraction of the light emitted by the LED is incident on the light sensitive photocathode of the PMT. The PMT output signal is checked against a reference that was set at the time of the last calibration. The gain of the PMT is adjusted if the measured signal has strayed from the reference.

This gain calibration technique depends on the light emitting diodes having a constant light output for each pulse. Light emitting diodes, however, do not have constant light output as a function of temperature, and may also vary over the lifetime of the diode. Another drawback of this technique of automatic calibration is that the light from the diode is mostly directly incident on the photocathode of the photomultiplier tube. Therefore, the transport of the light through the scintillation crystal, and associated optical elements, is not significantly sampled by the pulse of light from the diode.

User initiated quality control procedures usually require the placement of a radioactive source to uniformly illuminate the camera. The system acquires an appropriate number of events to achieve statistically significant sampling of each event location. A computer program then analyzes the measured energies and/or image of event locations to determine whether or not the system has drifted away from the properly calibrated state. Many variations of this procedure are possible, but all require the user to position a source of radioactivity and initiate the computer controlled acquisition and analysis. Additionally, the procedures also typically require the user to remove the collimator from the camera.

Quality control procedures are cumbersome to the user. If they can be initiated at the end of the day, and complete themselves automatically, then the user's time required is minimal. However, radioactive sources that must be left out in a room overnight require institutional procedures for securing the room, logging out the source and returning it in the morning, and prohibiting access to the room by cleaning and unauthorized personnel. Performing quality control procedures during working hours reduces available patient imaging time on the system and increases costs because personnel are not doing patient imaging.

Thus, it is desired to have a more reliable, cost effective means to troubleshoot and performance test any one or all of the detectors of a Gamma camera.

SUMMARY OF THE INVENTION

The embodiments of the present invention overcome the problems and disadvantages associated with current strategies and designs and provides new tools and methods for troubleshooting and performance testing of components in a Gamma camera.

One embodiment of the invention is directed to a method for testing a detector of a Gamma camera comprising the steps of forming, such as by using a field programmable gate array, digital words that replicate typical output signals of a photomultiplier tube, converting the digital words into an analog voltage, amplifying and applying the analog voltage to an analog multiplexer, injecting the pulse from the multiplexer into an input circuit of the detector, integrating the pulse into a current on the same order of magnitude as a photomultiplier tube output signal, and determining if the pulse is in a range for proper operation of the Gamma camera.

Preferably, the digital words are stored in a test pattern generator memory area of the field programmable gate array, the digital words are converted into an analog voltage by a high speed digital-to-analog converter, and the analog voltage being amplified and also applied to other solid state switches located near the circuitry of the detector. Preferably, the voltage signal is converted from the pulse injector into a current signal by addition of a high impedance in the signal path. Preferably, integrating the pulse into a current on the same order of magnitude as a photomultiplier tube output signal is performed by the processing circuits of the detector, and solid state switches installed at the detector signal path are left open during normal operation of the detector to prevent distortion. Preferably, the Gamma camera comprises a collimator, a scintillation crystal, a light guide, a photomultiplier tube, and an electronic circuit. In a preferred embodiment, the circuit being tested is a preamplifier. In another embodiment, the circuit being tested is a flash amplifier.

Another embodiment of the invention is directed to a system for performance testing a detector of a Gamma camera comprising a field programmable gate array for storing digital words to be converted to a pulse, a test pattern generator for forming the digital words, a digital-to-analog converter for converting outputted digital words into an analog voltage, an amplifier for amplifying the analog voltage, and an analog multiplexor for applying the analog voltage to an input circuit of the detection circuitry of the Gamma camera. It is preferred that the Gamma camera being tested comprises a collimator, a scintillation crystal, a light guide, a photomultiplier tube, and an electronic circuit. In a preferred embodiment, the electronic circuit is a preamplifier wherein the pulse is injected. In another embodiment, the electronic circuit is a flash amplifier wherein the pulse is injected.

Other embodiments and advantages of the invention are set forth in part in the description, which follows, and in part, may be apparent from this description, or may be learned from the practice of the invention.

DETAILED DESCRIPTION OF EXEMPLARY EMBODIMENTS

As embodied and broadly described herein, the embodiments of the present invention are directed to performance testing of detectors in a Gamma camera by adding a pulse injection circuit to the camera.

Figure 1:
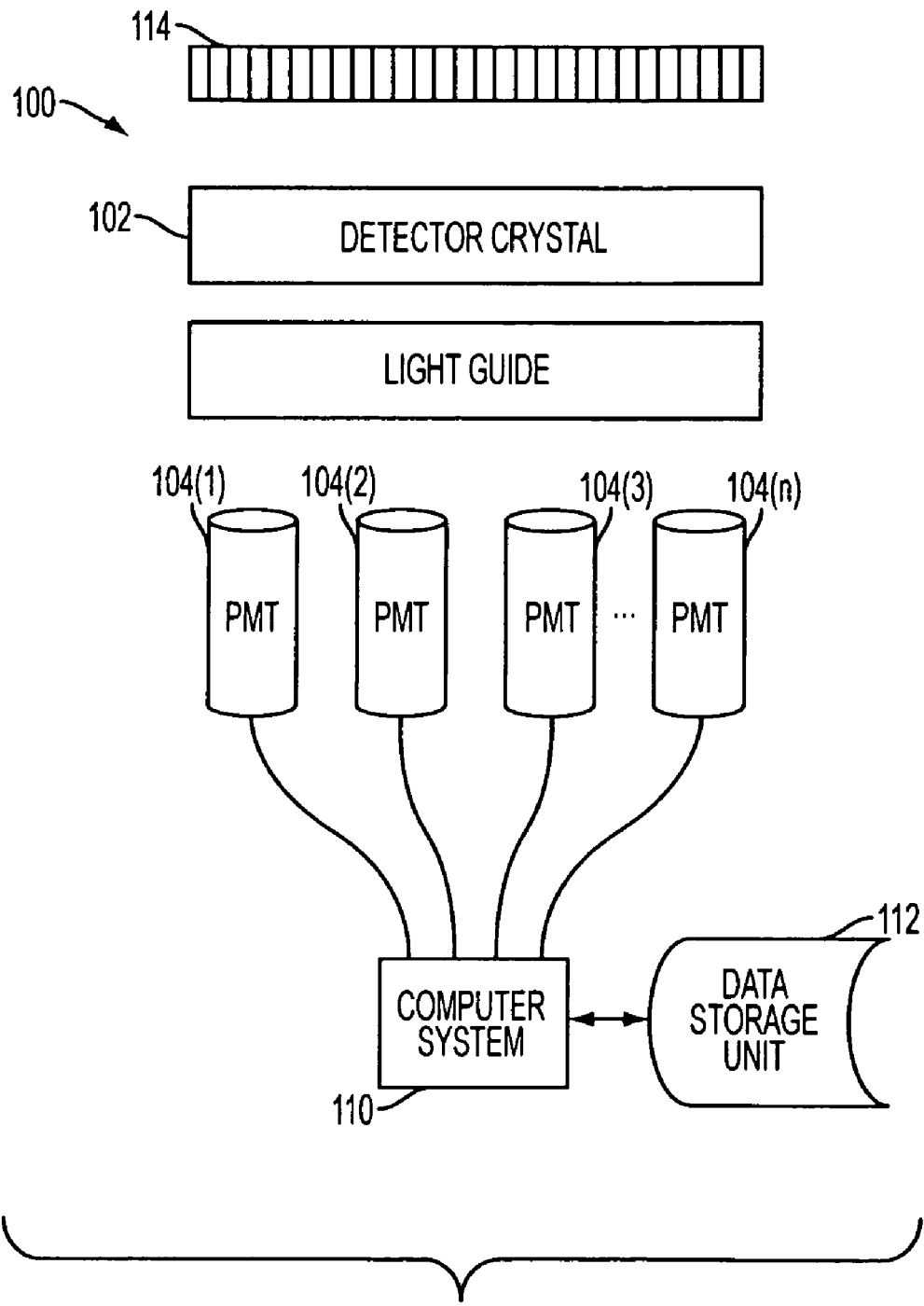
FIG. 1 (prior art) is a block diagram depiction of a typical Gamma camera.

FIG. 1 (prior art) is a diagram illustrating certain components of a Gamma camera 100 of a type applicable to one embodiment of the present invention. As shown in FIG. 1, Gamma camera 100 includes a scintillation crystal 102 (or "detector crystal 102"), a number of photomultiplier tubes (PMTs) 104(1) ... (n), and a computer system 110 coupled to the output of each PMT 104. Gamma camera 100 preferably includes a collimator 114. In other embodiments, a light guide 116 and a data storage unit 112 may be included.

In a preferred embodiment, a scintillation crystal, preferably NaI with thallium, emits light when struck by Gamma rays and the light is converted to an electrical signal by a photomultiplier tube 104. As shown in FIG. 1, an array of photomultipliers is typically positioned on the opposite side of the scintillation crystal 102 for receiving flashes of light emitted by the crystal in response to the incident radiant energy. Typically, the measure of light energy received by each photomultiplier is obtained by integrating circuits coupled to each of the photomultipliers, the relative magnitudes of these energies indicate the location of each of the light flashes on the crystal.

The stored energy of each of the photomultipliers is converted to a signal suitable for combining with the signals obtained from the energies of the other photomultipliers. In particular, it is noted that a highly active source of high energy radiation rapidly illuminates the scintillation crystal 102 with successive photons of high radiant energy such as the energy of x-rays or Gamma rays. Such rapid illumination is useful in obtaining high resolution images of the source, provided that the electronic circuitry utilized in forming pulse signals from the energy obtained from the photomultipliers is capable of operating at a rate commensurate with the rate at which high energy photons are incident upon the scintillation crystal.

Because precision is important to analysis, each circuit component, or detector, must be quality control tested often. It may be a faulty PMT, scintillation crystal, or electronic amplifier and/or associated circuits in a Gamma camera that need to be detected in the most cost efficient manner. The transfer function of the PMT has been studied and the output signal of a PMT can be replicated using a digital to analog converter (DAC), waveform memory, amplifier and solid state switches. Using state of the art electronic components, a pulse injection circuit can be added to an existing Gamma camera detector, providing a method for calibration and diagnostics of camera electronics in the absence of a gamma-ray source conventionally used for calibration.

Figure 2:
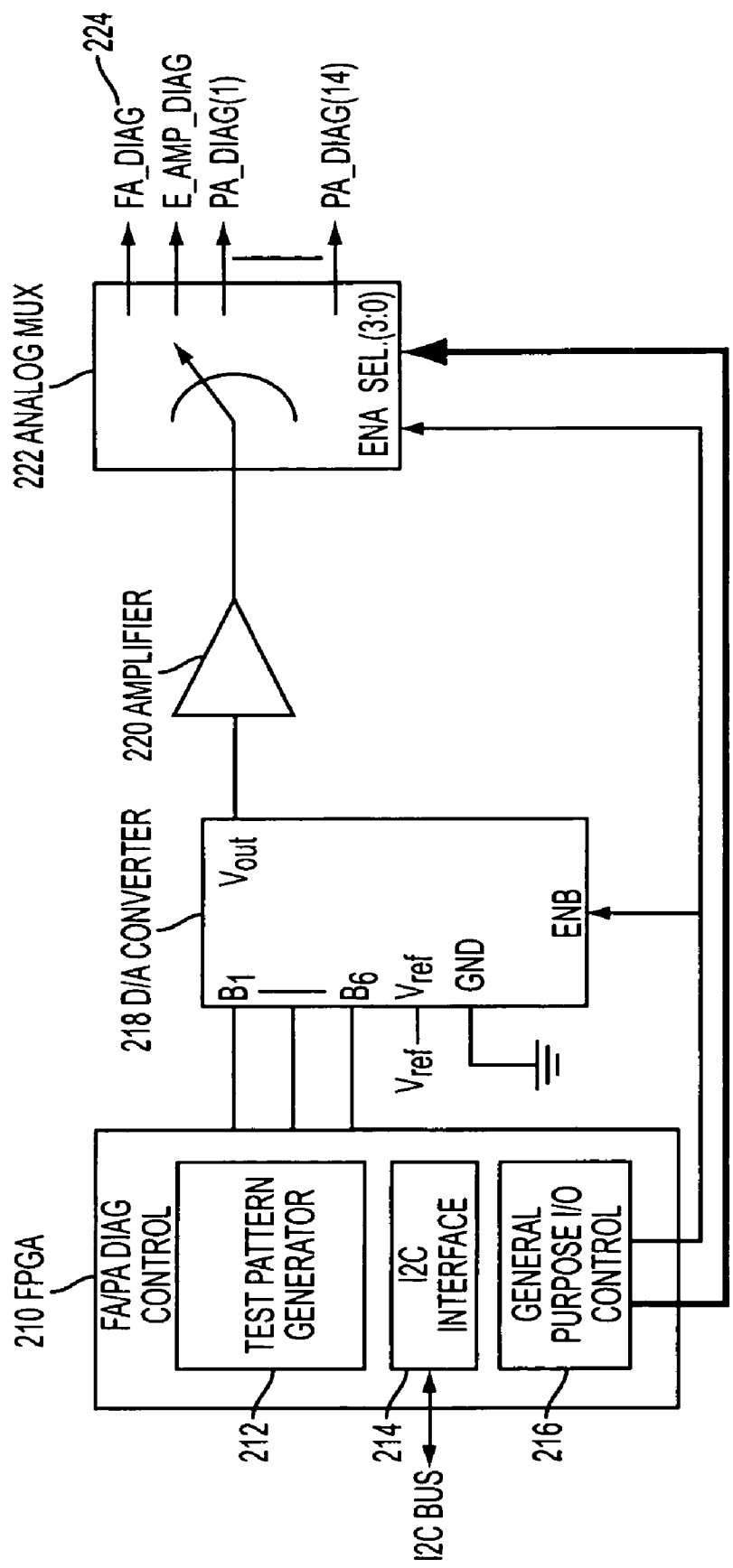
FIG. 2 is a block diagram of a circuit for generating and applying pulse to circuits in a Gamma camera detector according to an embodiment of the invention.

The preferred process for generating and applying the pulse to the circuits to be tested in a Gamma camera is depicted in FIG. 2. In a preferred embodiment, the camera circuitry 224 to be tested includes preamplifiers (PA-1-PA-14), a flash amplifier (FA), and/or other amplifier circuits ($E_{13}$ AMP). The charge-sensitive preamplifier (PA-1-PA-14) associated with each PMT can be stand-alone or incorporated into the PMT base. A pulse is injected into the PA or FA circuits, which can be formed by digital words stored in the memory area of test pattern generator 212 of a field programmable gate array (FPGA) 210.

Test pattern generator 212 can be used to generate a number of different output signal patterns that replicate PMT responses to scintillation events caused by interaction of gamma photons from various sources and/or concentrations of gamma radiation with a scintillation crystal. The signal patterns may be represented by particular output sequences of digital words read out from the memory area of the test pattern generator 212. Each sequence may be separately stored, such that generation of the signal pattern may be obtained by recalling a particular sequence and then reading out in succession each digital word identified in the sequence. In this way, calibration and diagnostic testing may be performed for a variety of different gamma sources and/or different concentrations of gamma sources as may be administered to a patient.

Field programmable gate array (FPGA) 210, whether alone, or forming an embedded portion of a system-on-chip or other application specific integrated circuit, is a type of integrated circuit consisting of an array of programmable logic blocks interconnected by a programmable interconnect or routing network and programmable input/output cells. Such blocks of the FPGA may include an I2C (ie., inter-IC) bus 214 and a general purpose I/O control unit 216. The I2C bus 214 is a known bi-directional two-wire serial bus that provides a communication link between integrated circuits. Programming of logic blocks, the interconnect resources which make up the network, and the input/output cells is selectively completed to make the necessary interconnections that establish one configuration thereof to provide the desired system operation/function for a particular application. Off-line methods of built-in self-testing of the array of programmable logic blocks and the programmable interconnect resources in FPGAs at device, board and system levels are known.

A high speed digital analog converter (DAC) 218 converts the digital words outputted from FPGA 210 into an analog voltage at its output. The DAC preferably has a clocking speed of 40 megasamples per second or greater. An amplifier 220 amplifies and applies the analog voltage to an analog multiplexor (MUX) 222 and other solid state switches (not shown) located near the PA and FA circuitry. Because the PMT output is a current signal, the addition of a high impedance in the path of the PA and FA circuits converts the voltage signal from the MUX 222 into a current signal of the same order of magnitude as that from a PMT. During use of the pulse injection circuit the processing circuits of the detector can integrate the injected pulse signal as applied to the amplifier inputs and determine if it is within a range of proper operation of the camera.

If the integrated signal is not within such a range, this would indicate that one or more of the PAs, FAs, or processing circuits is faulty and needs to be repaired or replaced.

Solid state switches are installed between the pulse injection circuit and each PA and FA signal path. These switches are placed in an open or high impedance state during normal operation of the Gamma camera detector. This prevents any possible distortion of the normal signals due to the presence of the pulse injection circuitry.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

The invention having been described, it will be apparent to those skilled in the art that the same may be varied in many ways without departing from the spirit and scope of the invention. Any and all such modifications are intended to be included within the scope of the following claims.

What is claimed is:

1. A method for calibration and/or testing of a gamma camera comprising the steps of:

forming a replica of an output signal of a photodetector of said gamma camera;

injecting said replica into an input of a photodetector signal processing circuit of said gamma camera;

processing said replica in said processing circuit to develop a processing circuit output signal; and comparing said processing circuit output signal with a reference signal to determine whether said gamma camera is calibrated and/or operating properly, wherein said forming step further comprises forming a plurality of digital words in a field programmable gate array, convening the digital words into an analog voltage pulse, and amplifying the analog voltage pulse and applying the amplified analog voltage pulse to a multiplexer.

2. A method for calibration and/or testing of a gamma camera as set forth in claim 1, wherein said injecting step comprises the step of injecting the pulse from said multiplexer into a selected signal processing circuit of the gamma camera.

3. A method for calibration and/or testing of a gamma camera as set forth in claim 2, wherein said processing step comprises the step of integrating the pulse into an integrated signal.

4. A method for calibration and/or testing of a gamma camera as set forth in claim 3, wherein said comparing step comprises the step of determining if the pulse is within a range for proper operation of the gamma camera.

5. A method for calibration and/or testing of a gamma camera as set forth in claim 3, wherein converting the voltage signal into a current signal further comprises addition of a high impedance in a signal path of said voltage signal.

6. A method for calibration and/or testing a detector of a gamma camera as set forth in claim 1, wherein the digital words are stored in a test pattern generator memory area of the field programmable gate array.

7. A method for calibration and/or testing of a gamma camera as set forth in claim 1, wherein converting the digital words into an analog voltage is performed by a high speed digital-to-analog converter.

8. A method for calibration and/or testing of a gamma camera as set forth in claim 1 wherein said analog voltage is further amplified and applied to other solid state switches proximate to the signal processing circuitry of the detector.

9. A method for calibration and/or testing of a gamma camera as set forth in claim 1, further comprising the step of placing a solid state switch installed in a signal path of said photodetector signal processing circuit in an open state during normal operation of the gamma camera.

10. A method for calibration and/or testing of a gamma camera as set forth in claim 1, wherein the gamma camera comprises a collimator, a scintillation crystal, at least one photomultiplier tube, and an electronic signal processing circuit.

11. A method for calibration and/or testing of a gamma camera as set forth in claim 1. wherein the photodetector signal processing circuit comprises a preamplifier.

12. A system for performance testing of a gamma camera, comprising:
- a field programmable gate array configured to form and store digital words to be converted to a pulse;
- a test pattern generator configured to generate the digital words;
- a digital-to-analog converter configured to convert the digital words into an analog voltage;
- an amplifier configured to amplify and apply the analog voltage;
- and an analog multiplexer configured to accept the analog voltage,
- wherein the gamma camera comprises a collimator, a scintillation crystal, a light guide, a photomultiplier tube, and an electronic circuit.

13. A system for performance testing of a gamma camera as set forth in claim 12, wherein the electronic circuit is a preamplifier wherein the pulse is injected.

* * * * *